United States Patent
Morikawa et al.

(10) Patent No.: US 10,702,168 B2
(45) Date of Patent: Jul. 7, 2020

(54) BLOOD PRESSURE ESTIMATION APPARATUS, BLOOD PRESSURE ESTIMATION METHOD, AND NON-TRANSITORY COMPUTER-READABLE RECORDING MEDIUM

(71) Applicant: Panasonic Intellectual Property Management Co., Ltd., Osaka (JP)

(72) Inventors: Koji Morikawa, Tokyo (JP); Koichi Ikemoto, Hyogo (JP); Masatoshi Sasaki, Osaka (JP); Satoshi Kanai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 379 days.

(21) Appl. No.: 15/795,468

(22) Filed: Oct. 27, 2017

(65) Prior Publication Data
US 2018/0055388 A1    Mar. 1, 2018

Related U.S. Application Data

(63) Continuation of application No. PCT/JP2017/014495, filed on Apr. 7, 2017.

(30) Foreign Application Priority Data

May 19, 2016  (JP) ................................. 2016-100082
Mar. 1, 2017  (JP) ................................. 2017-038668

(51) Int. Cl.
    A61B 5/021    (2006.01)
    A61B 5/0452   (2006.01)
    (Continued)

(52) U.S. Cl.
    CPC ........ *A61B 5/02108* (2013.01); *A61B 5/0245* (2013.01); *A61B 5/02125* (2013.01);
    (Continued)

(58) Field of Classification Search
    CPC ......... A61B 5/021; A61B 5/00; A61B 5/0245; A61B 5/02108; A61B 5/0452;
    (Continued)

(56) References Cited

U.S. PATENT DOCUMENTS

2007/0016085 A1    1/2007    Inukai et al.
2007/0185393 A1    8/2007    Zhou et al.
(Continued)

FOREIGN PATENT DOCUMENTS

CN    101327121    12/2008
JP    2007-007075    1/2007
(Continued)

OTHER PUBLICATIONS

International Search Report of PCT application No. PCT/JP2017/014495 dated Jun. 13, 2017.
(Continued)

*Primary Examiner* — Eric J Messersmith
(74) *Attorney, Agent, or Firm* — Wenderoth, Lind & Ponack, L.L.P.

(57) ABSTRACT

A blood pressure estimation apparatus includes: a pulse wave measurement unit measuring a user's pulse wave signal; an electrocardiogram signal measurement unit measuring a user's electrocardiogram signal; and a processing circuit estimating a user's blood pressure value by using the pulse wave and electrocardiogram signals, wherein the processing circuit (a) acquires a pulse wave signal feature by using the pulse wave signal, (b) acquires an electrocardiogram signal feature by using the electrocardiogram signal, (c) acquires a pulse wave propagation time by using the
(Continued)

pulse wave and electrocardiogram signals, (d) selects a blood pressure group indicating a relationship between a pulse wave propagation time and blood pressure of the user by using the pulse wave signal feature, electrocardiogram signal feature, and pulse wave propagation time, and (e) estimates the blood pressure value by using the blood pressure group, pulse wave signal feature, electrocardiogram signal feature, and pulse wave propagation time.

14 Claims, 13 Drawing Sheets

(51) Int. Cl.
*A61B 5/00* (2006.01)
*A61B 5/024* (2006.01)
*A61B 5/0245* (2006.01)
*A61B 5/0404* (2006.01)
*A61B 5/0408* (2006.01)

(52) U.S. Cl.
CPC ........ *A61B 5/02416* (2013.01); *A61B 5/0452* (2013.01); *A61B 5/6826* (2013.01); *A61B 5/7278* (2013.01); *A61B 5/02116* (2013.01); *A61B 5/0404* (2013.01); *A61B 5/0408* (2013.01); *A61B 5/726* (2013.01); *A61B 5/7267* (2013.01); *A61B 5/7275* (2013.01)

(58) Field of Classification Search
CPC ............ A61B 5/02125; A61B 5/02416; A61B 5/6826; A61B 5/7278; A61B 5/726; A61B 5/7267; A61B 5/02116; A61B 5/7275; A61B 5/0404; A61B 5/0408
See application file for complete search history.

(56) References Cited

U.S. PATENT DOCUMENTS

2014/0142441 A1    5/2014  Fuke et al.
2018/0085011 A1*   3/2018  Ma ...................... A61B 5/7203

FOREIGN PATENT DOCUMENTS

JP    2008-302127    12/2008
JP    2009-089829     4/2009
JP    2010-220690    10/2010

OTHER PUBLICATIONS

Yoshifumi Kishimoto et al., "Cuffless Blood Pressure Estimation with Pulse Wave Signal Analysis by Means of Non-linear Regression Method", IEICE, vol. J98-A, No. 2, pp. 200-208, Feb. 2015.
Koichi Fujimoto et al., "Application of Accelerated Plethysmography for Measuring Pulse Wave Velocity", Japan Ergonomics Society, vol. 48, No. 6, pp. 285-294, Mar. 2013.
Extended European Search Report dated Apr. 11, 2019 in European Patent Application No. 17791533.7.

* cited by examiner

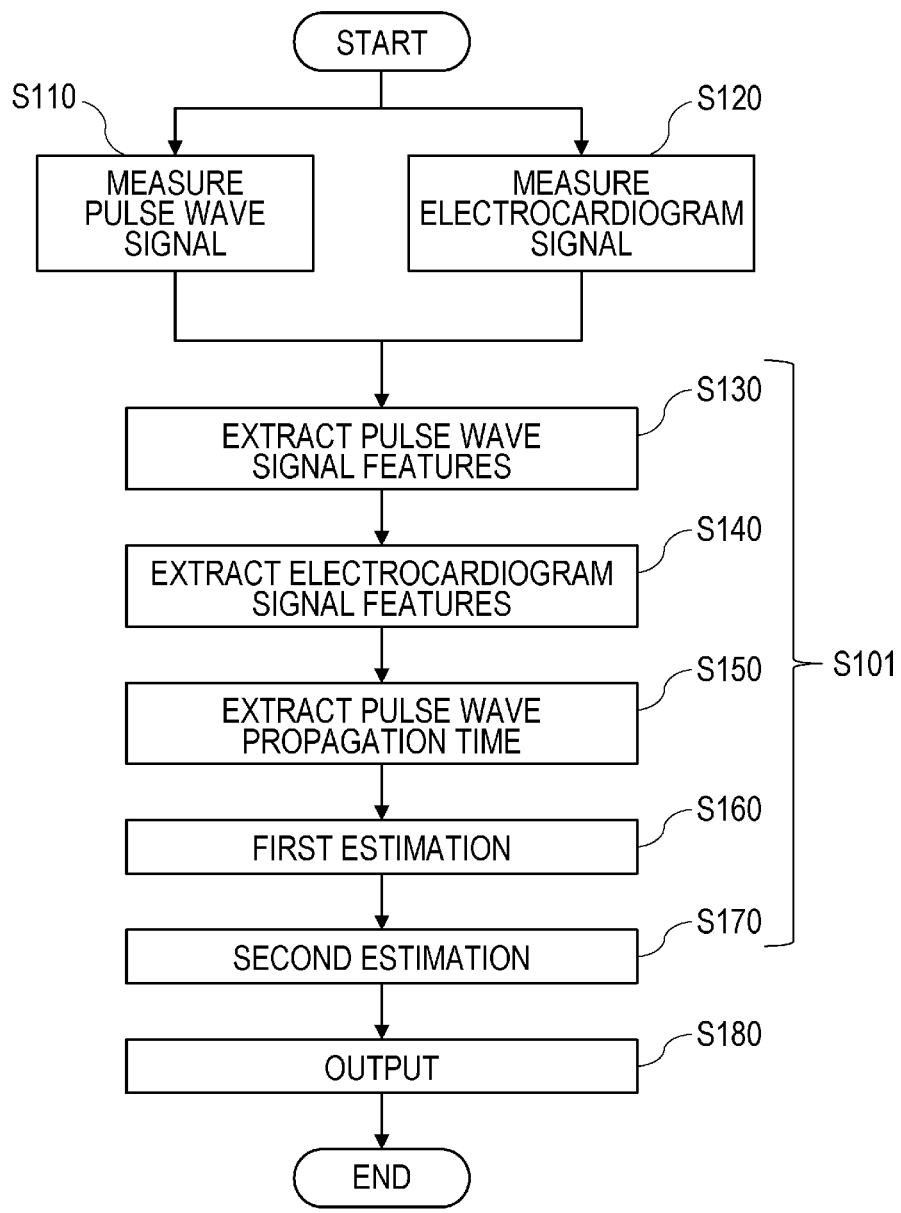

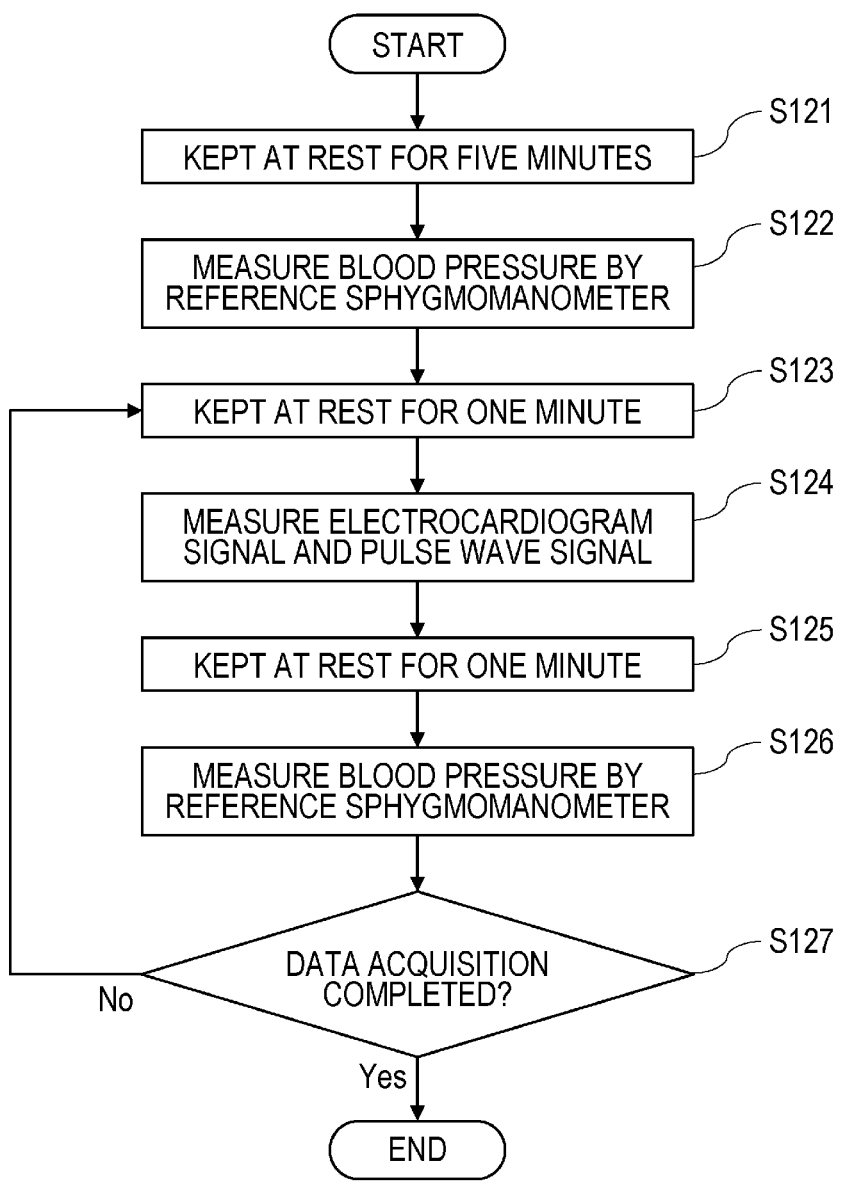

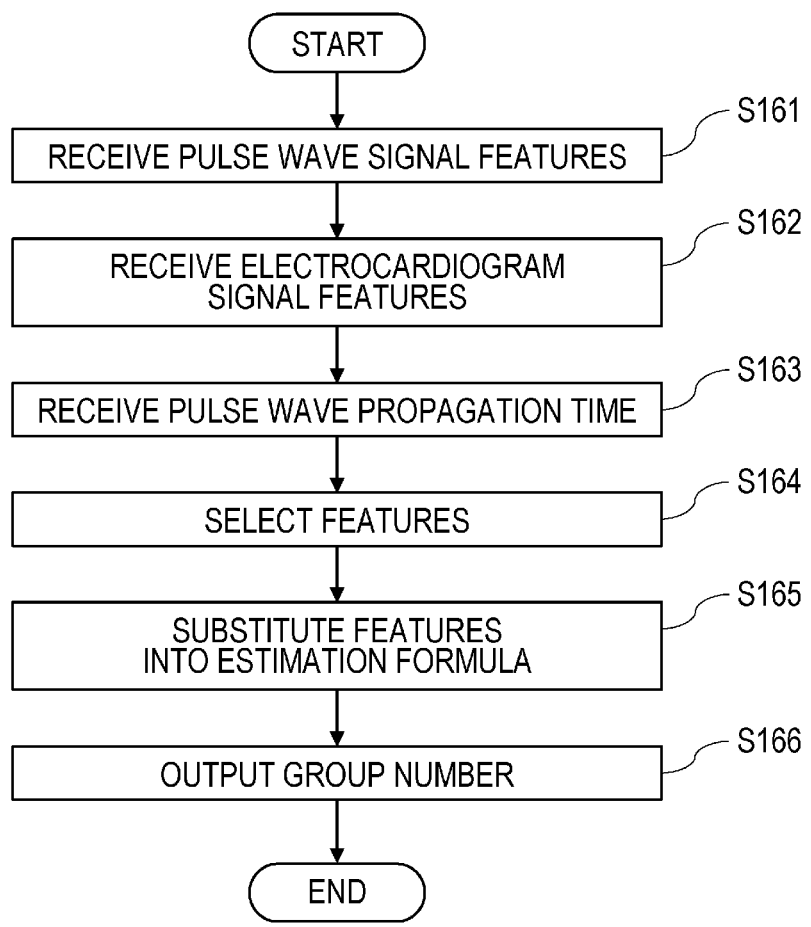

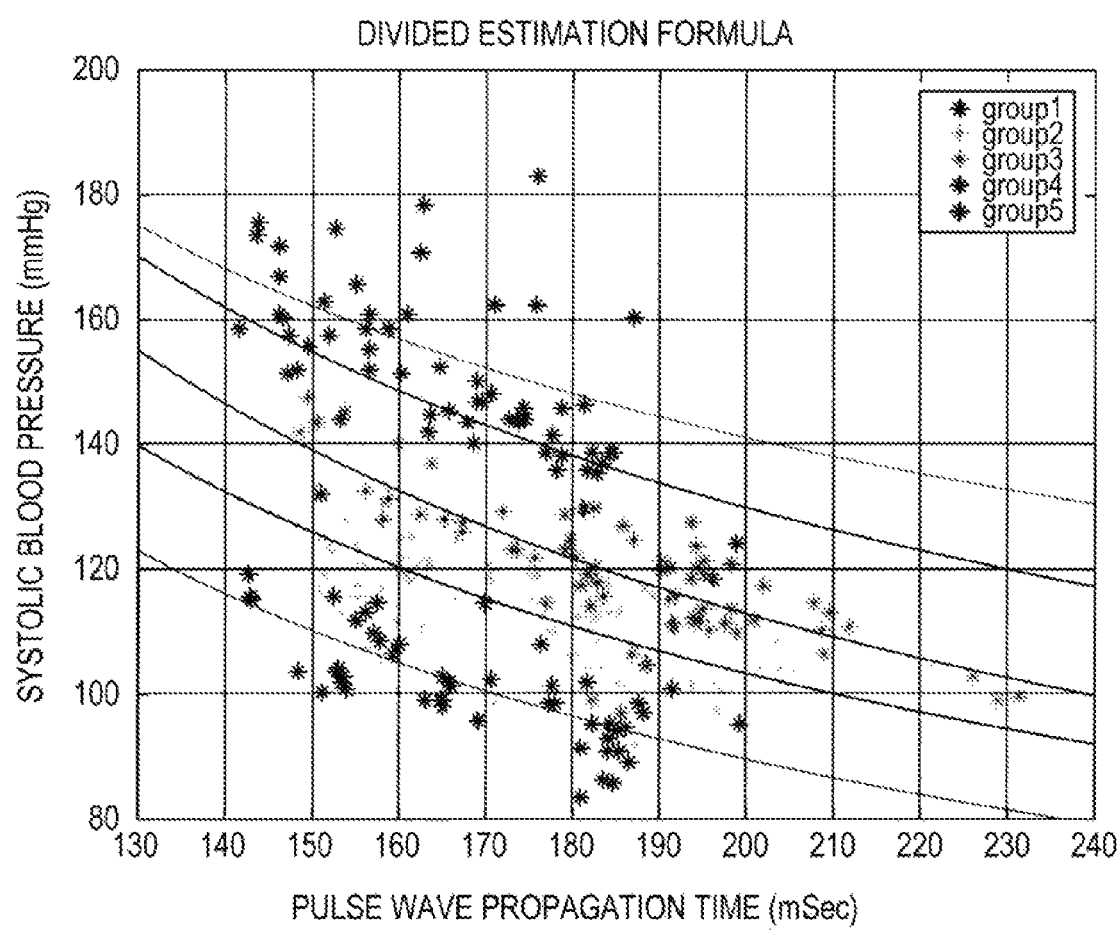

BLOOD PRESSURE ESTIMATION APPARATUS, BLOOD PRESSURE ESTIMATION METHOD, AND NON-TRANSITORY COMPUTER-READABLE RECORDING MEDIUM

BACKGROUND

1. Technical Field

The present disclosure relates to a blood pressure estimation apparatus, a blood pressure estimation method, and a non-transitory computer-readable recording medium.

2. Description of the Related Art

In recent years, attempts to accumulate user's health-care related information and manage a user's health condition by using an IT device have been increasingly made. As for measurement of blood pressure, daily measurement and recording are recommended especially to those who have high blood pressure and require health management. However, in a current situation in which cuff-type sphygmomanometers are used, users fail in continuous recording of blood pressure in many cases, for example, because of a trouble of attaching a cuff and users' feel of compression at a cuff attachment part. In order to address these problems, simplified methods for estimating blood pressure without attachment of a cuff have been considered.

A blood pressure measurement apparatus disclosed in Japanese Unexamined Patent Application Publication No. 2007-007075 measures a blood pressure value by using a pulse wave propagation time. The blood pressure measurement apparatus disclosed in Japanese Unexamined Patent Application Publication No. 2007-007075 utilizing correlation between a blood pressure value and a pulse wave propagation time that is calculated by using a pulse wave signal and an electrocardiogram signal included in an electrocardiogram.

Yoshifumi KISHIMOTO, Haruki KAWANAKA, and Koji OGURI "Cuffless Blood Pressure Estimation with Pulse Wave Signal Analysis by Means of Non-linear Regression Method", The transactions of The Institute of Electronics, Information and Communication Engineers A, Vol. J98-A, No. 2, pp. 200-208, 2015 attempts an improvement of estimation accuracy by using a support vector machine as a non-linear regression method.

According to the conventional arts, sufficient accuracy cannot be obtained in measurement of a blood pressure value without a cuff.

SUMMARY

In one general aspect, the techniques disclosed here feature a blood pressure estimation apparatus including: a pulse wave measurement unit that measures a pulse wave signal of a user; an electrocardiogram signal measurement unit that measures an electrocardiogram signal of the user; and a processing circuit that estimates a blood pressure value of the user by using the pulse wave signal of the user and the electrocardiogram signal of the user, wherein the processing circuit (a) acquires a pulse wave signal feature by using the pulse wave signal of the user, (b) acquires an electrocardiogram signal feature by using the electrocardiogram signal of the user, (c) acquires a pulse wave propagation time by using the pulse wave signal of the user and the electrocardiogram signal of the user, (d) selects a blood pressure group indicative of a relationship between a pulse wave propagation time and blood pressure of the user by using the pulse wave signal feature, the electrocardiogram signal feature, and the pulse wave propagation time, and (e) estimates the blood pressure value of the user by using the blood pressure group, the pulse wave signal feature, the electrocardiogram signal feature, and the pulse wave propagation time.

According to the blood pressure estimation apparatus, blood pressure estimation method, and non-transitory computer-readable recording medium, it is possible to improve accuracy of estimation of a blood pressure value.

It should be noted that general or specific embodiments may be implemented as a device, a system, a method, an integrated circuit, a computer program, a computer-readable recording medium, or any selective combination thereof. The computer-readable recording medium includes non-volatile recording medium such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 illustrates a flow of overall processing of a blood pressure estimation method;

FIG. 4 illustrates a flow of an experiment of acquisition of data for evaluation;

FIG. 7 illustrates a processing flow of a first estimation unit;

FIG. 11 illustrates linear formulas for respective groups;

DETAILED DESCRIPTION

Figure 1:
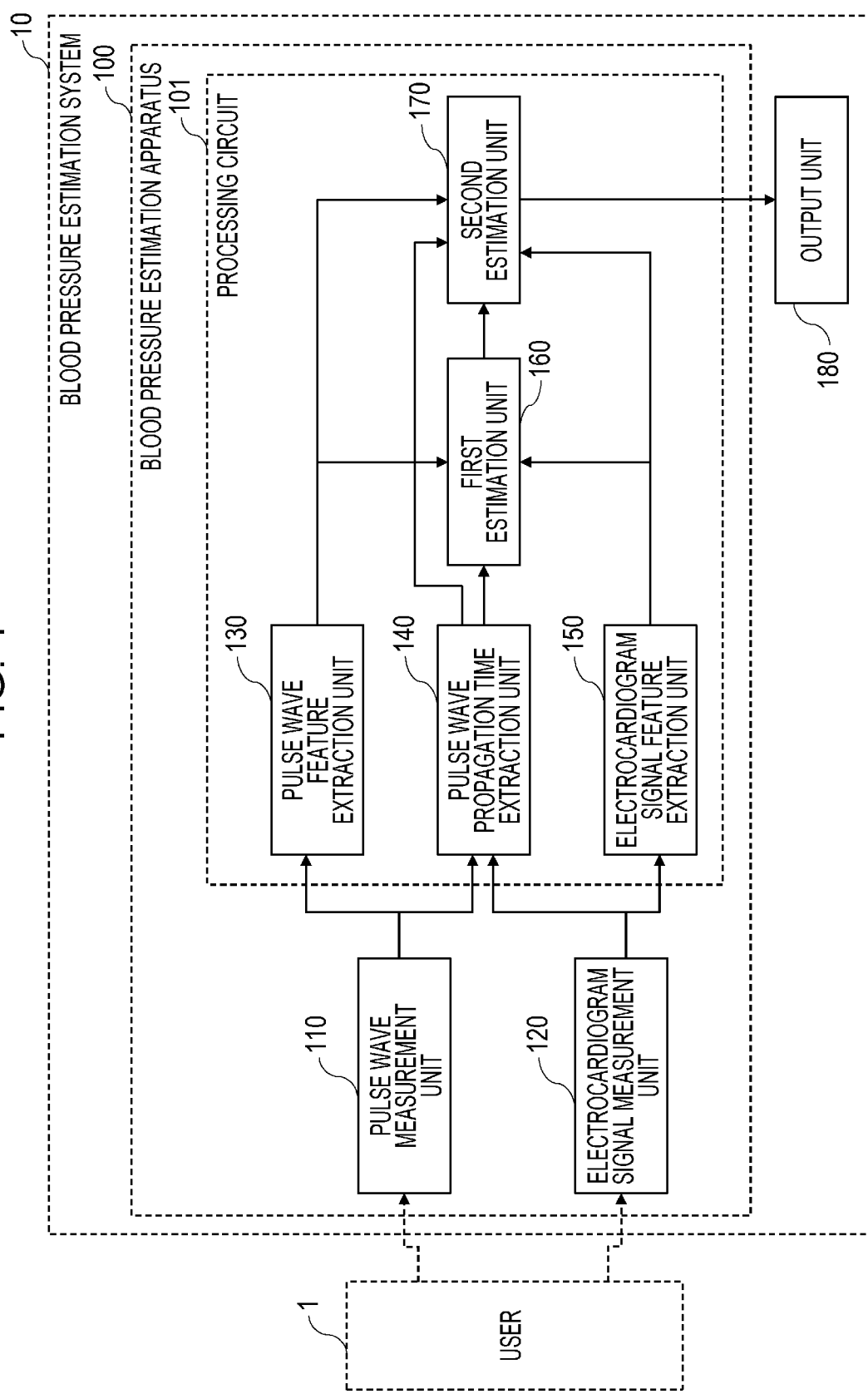
FIG. 1 illustrates a configuration of a blood pressure estimation apparatus according to an embodiment.

Various aspects of the present disclosure are described before detailed description of an embodiment according to the present disclosure.

A blood pressure estimation apparatus according to an aspect of the present disclosure includes: a pulse wave measurement unit that measures a pulse wave signal of a user; an electrocardiogram signal measurement unit that measures an electrocardiogram signal of the user; and a processing circuit that estimates a blood pressure value of the user by using the pulse wave signal of the user and the electrocardiogram signal of the user, wherein the processing circuit (a) acquires a pulse wave signal feature by using the pulse wave signal of the user, (b) acquires an electrocardiogram signal feature by using the electrocardiogram signal of the user, (c) acquires a pulse wave propagation time by using the pulse wave signal of the user and the electrocardiogram signal of the user, (d) selects a blood pressure group indicative of a relationship between a pulse wave propagation time and blood pressure of the user by using the pulse wave signal feature, the electrocardiogram signal feature, and the pulse wave propagation time, and (e) estimates the blood pressure value of the user by using the blood pressure group, the pulse wave signal feature, the electrocardiogram signal feature, and the pulse wave propagation time.

The blood pressure estimation apparatus may be configured such that the blood pressure group includes a first group having a first blood pressure value with respect to the pulse wave propagation time and a second group having a blood pressure value lower than the first blood pressure value with respect to the pulse wave propagation time; and in (d), the processing circuit selects the first group or the second group by using the pulse wave signal feature, the electrocardiogram signal feature, and the pulse wave propagation time.

The blood pressure estimation apparatus may be configured such that the processing circuit acquires a pulse wave wavelet feature by using the pulse wave signal of the user in (a) and acquires an electrocardiogram wavelet feature by using the electrocardiogram signal of the user in (b).

The blood pressure estimation apparatus may be configured such that the processing circuit acquires a pulse wave wavelet feature by using a pulse wave waveform corresponding to a single heartbeat of the user in (a) and acquires an electrocardiogram wavelet feature by using an electrocardiogram waveform corresponding to a single heartbeat of the user in (b).

The blood pressure estimation apparatus may be configured such that in (e), the processing circuit acquires an estimation rule corresponding to the blood pressure group and estimates the blood pressure value of the user by using the estimation rule, the pulse wave signal feature, the electrocardiogram signal feature, and the pulse wave propagation time.

The blood pressure estimation apparatus may be configured such that the estimation rule is an estimation formula using the pulse wave signal feature, the electrocardiogram signal feature, and the pulse wave propagation time as variables; and in (e), the processing circuit estimates the blood pressure value of the user by using the pulse wave signal feature, the electrocardiogram signal feature, and the pulse wave propagation time while referring to the estimation formula.

The blood pressure estimation apparatus may be configured to further include an output unit that outputs the estimated blood pressure value.

A non-transitory computer-readable recording medium according to an aspect of the present disclosure is a non-transitory computer-readable recording medium storing a program for causing a computer to: (f1) acquire a pulse wave signal of a user and an electrocardiogram signal of the user, (f2) acquire a pulse wave signal feature by using the pulse wave signal of the user, (f3) acquire an electrocardiogram signal feature by using the electrocardiogram signal of the user, (f4) acquire a pulse wave propagation time by using the pulse wave signal of the user and the electrocardiogram signal of the user, (f5) select a blood pressure group indicative of a relationship between a pulse wave propagation time and blood pressure of the user by using the pulse wave signal feature, the electrocardiogram signal feature, and the pulse wave propagation time, and (f6) estimate a blood pressure value of the user by using the blood pressure group, the pulse wave signal feature, the electrocardiogram signal feature, and the pulse wave propagation time.

A blood pressure estimation method according to an aspect of the present disclosure includes (f1) acquiring a pulse wave signal of a user and an electrocardiogram signal of the user; (f2) acquiring a pulse wave signal feature by using the pulse wave signal of the user; (f3) acquiring an electrocardiogram signal feature by using the electrocardiogram signal of the user; (f4) acquiring a pulse wave propagation time by using the pulse wave signal of the user and the electrocardiogram signal of the user; (f5) selecting a blood pressure group indicative of a relationship between a pulse wave propagation time and blood pressure of the user by using the pulse wave signal feature, the electrocardiogram signal feature, and the pulse wave propagation time; and (f6) estimating a blood pressure value of the user by using the blood pressure group, the pulse wave signal feature, the electrocardiogram signal feature, and the pulse wave propagation time. A blood pressure measurement apparatus according to an aspect of the present disclosure includes a pulse wave measurement sensor that measures a first pulse wave signal of a first user and a second pulse wave signal of a second user; an electrocardiogram signal measurement sensor that measures a first electrocardiogram signal of the first user and a second electrocardiogram signal of the second user, and a processing circuit including a memory, wherein the memory includes first information including $w1(0), w1(1), \ldots, w1(j), \ldots w1(j+k)$, second information including $w2(0), w2(1), \ldots, w1(j), \ldots w2(j+k)$, third information including $w3(0), w3(1), \ldots, w1(j), \ldots w3(j+k)$, and fourth information including $w4(0), w4(1), \ldots, w1(j), \ldots w4(j+k)$ where j is a natural number and k is a natural number, wherein the processing circuit (a-1) acquires pulse wave signal features $x1(1), \ldots, x1(j)$ by performing wavelet transform of the first pulse wave signal, (a-2) acquires electrocardiogram features $x1(j+1), \ldots, x1(j+k)$ by performing wavelet transform of the first electrocardiogram signal, (a-3) calculates a first pulse wave propagation time $x1(0)$ that is a difference between a first time of a peak included in a first period of the first pulse wave signal and a second time of a peak included in a second period of the first electrocardiogram signal, (a-4) calculates $w1(0) \times x1(0) + w1(1) \times x1(1) + \ldots + w1(j) \times x1(j) + w1(j+1) \times x1(j+1) + \ldots + w1(j+k) \times x1(j+k)$ that is a first result and determines whether the first result belongs to a first group, (a-5) calculates $w3(0) \times x1(0) + w3(1) \times x1(1) + \ldots + w3(j) \times x1(j) + w3(j+1) \times x1(j+1) + \ldots + w3(j+k) \times x1(j+k)$ that is a second result in a case where the first result belongs to the first group, (a-6) outputs the second result as a blood pressure value of the first user, (b-1) acquires pulse wave signal features $x2(1), \ldots, x2(j)$ by performing wavelet transform of the second pulse wave signal, (b-2) acquires electrocardiogram features $x2(j+1), \ldots, x2(j+k)$ by performing wavelet transform of the second electrocardiogram signal, (b-3) calculates a second pulse wave propagation time $x2(0)$ that is a different between a third time of a peak included in a third period of the second pulse wave signal and a fourth time of a peak included in the fourth period of the second electrocardiogram signal, (b-4) calculates $w1(0) \times x2(0) + w1(1) \times x2(1) + \ldots + w1(j) \times x2(j) + w1(j+1) \times x2(j+1) + \ldots + w1(j+k) \times x2(j+k)$ that is a third result and determines whether the third result belongs to the first group, (b-5) calculates $w2(0) \times x2(0) + w2(1) \times x2(1) + \ldots + w2(j) \times x2(j) + w2(j+1) \times x2(j+1) + \ldots + w2(j+k) \times x2(j+k)$ that is a fourth result in a case where the third result does not belong to the first group, (b-6) calculates $w4(0) \times x2(0) + w4(1) \times x2(1) + \ldots + w4(j) \times x2(j) + w4(j+1) \times x2(j+1) + \ldots + w4(j+k) \times x2(j+k)$ that is a fifth result in a case where the fourth result belongs to the second group, and (b-7) outputs the fifth result as a blood pressure value of the second user, and wherein the second result and the fifth result are different in a case where $x1(0)$ and $x2(0)$ are the same.

An embodiment of the present disclosure is described below with reference to the drawings.

Embodiment 1

FIG. 1 illustrates a configuration of a blood pressure estimation apparatus 100 according to Embodiment 1.

The blood pressure estimation apparatus 100 illustrated in FIG. 1 includes a processing circuit 101, a pulse wave measurement unit 110, and an electrocardiogram signal measurement unit 120. The processing circuit 101 includes a pulse wave feature extraction unit 130, a pulse wave propagation time extraction unit 140, an electrocardiogram signal feature extraction unit 150, a first estimation unit 160, and a second estimation unit 170. A blood pressure estimation system 10 includes the blood pressure estimation apparatus 100 and an output unit 180.

Details of Constituent Elements

Details of constituent elements are described below with reference to the drawings and results of experiments.

Outline of Apparatus

Figure 2A:
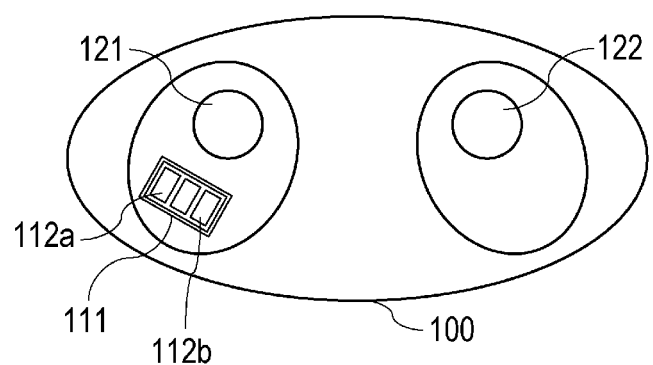
FIG. 2A illustrates external appearance of the blood pressure estimation apparatus according to the embodiment.
Figure 2B:
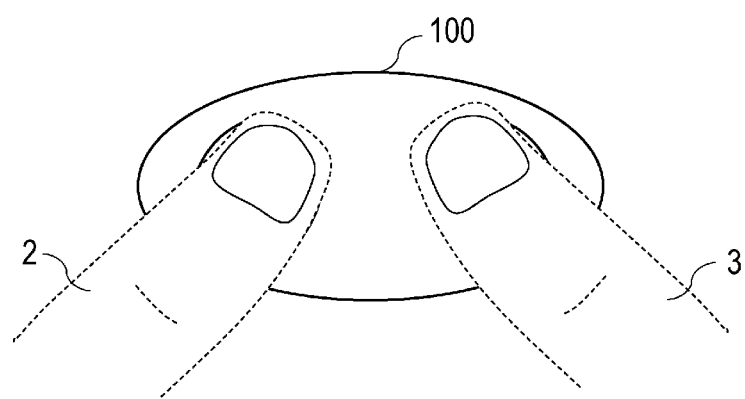
FIG. 2B illustrates a situation of measurement using the blood pressure estimation apparatus according to the embodiment.

FIGS. 2A and 2B illustrate an example of a form in which the blood pressure estimation apparatus 100 is realized. FIG. 2A illustrates an example of external appearance of the blood pressure estimation apparatus 100. The blood pressure estimation apparatus 100 illustrated in FIG. 2A has a housing. The blood pressure estimation apparatus 100 estimates blood pressure of a user 1 while the user 1 is in contact with the housing.

FIG. 2B illustrates how the blood pressure estimation apparatus 100 estimates blood pressure. The blood pressure estimation apparatus 100 illustrated in FIG. 2B is held by a finger 2 and a finger 3 of the user 1. The blood pressure estimation apparatus 100 illustrated in FIGS. 2A and 2B includes the pulse wave measurement unit 110 and the electrocardiogram signal measurement unit 120. The blood pressure estimation apparatus 100 can estimate blood pressure of the user 1 without a cuff. This will be described later in detail.

Pulse Wave Measurement Unit 110

The pulse wave measurement unit 110 measures a pulse wave signal of the user 1. The pulse wave signal of the user 1 includes information on at least one heartbeat. An example of hardware of the pulse wave measurement unit 110 is a pulse wave sensor.

The example of the pulse wave measurement unit 110 illustrated in FIG. 2A includes a light emitting unit 111 and light receiving units 112a and 112b. The light emitting unit 111 is a light source. An example of the light source is an LED. The light receiving units 112a and 112b are disposed close to the light emitting unit 111. For example, as illustrated in FIG. 2A, the light receiving units 112a and 112b are disposed so as to sandwich the light emitting unit 111.

In a case where the blood pressure estimation apparatus 100 is held by the thumb 2 and the thumb 3 of the user 1 as illustrated in FIG. 2B, the light emitting unit 111 emits light, and the light receiving units 112a and 112b detects light reflected by the user 1.

The light detected by the light receiving units 112a and 112b has information reflecting a condition of a blood flow in skin of the user 1. Light during a predetermined period detected by the light receiving units 112a and 112b includes a change of a condition of a blood flow of the user 1.

Electrocardiogram Signal Measurement Unit 120

The electrocardiogram signal measurement unit 120 measures an electrocardiogram signal of the user 1. The electrocardiogram signal of the user 1 is a signal based on a temporal change of a cardiac potential of the user 1 and includes information on at least one heartbeat. The electrocardiogram may include an electrocardiogram signal. An example of hardware of the electrocardiogram signal measurement unit 120 is an electrocardiograph sensor.

The electrocardiogram signal measurement unit 120 illustrated in FIG. 2A includes a plurality of electrodes 121 and 122. An example of the housing has a surface having recesses. The plurality of electrodes 121 and 122 are disposed in the recesses.

In FIG. 2A, the electrode 121 is in contact with the left hand of the user 1, and the electrode 122 is in contact with the right hand of the user 1. More specifically, the thumb 2 of the left hand is in contact with a left recess, and the thumb 3 of the right hand is in contact with a right recess.

The electrocardiogram signal measurement unit 120 acquires an electrocardiogram signal of the user 1 by measuring an electric potential difference between the plurality of electrodes 121 and 122. The electrocardiogram signal reflects a condition concerning heart movement (heartbeat).

Since the electrocardiogram signal measurement unit 120 and the pulse wave measurement unit 110 are disposed in the recesses or close to the recesses, the pulse wave measurement unit 110 makes contact with the user 1 and the user 1 makes contact with the electrodes 121 and 122 when the user 1 holds the housing.

Processing Circuit 101

The processing circuit 101 acquires pulse wave signal features, electrocardiogram signal features, and a pulse wave propagation time by using a pulse wave signal and an electrocardiogram signal obtained by measurement. The processing circuit 101 estimates a user's blood pressure group by using the pulse wave signal features, the electrocardiogram signal features, and the pulse wave propagation time. The blood pressure group will be described later.

The processing circuit 101 includes the pulse wave feature extraction unit 130, the pulse wave propagation time extraction unit 140, the electrocardiogram signal feature extraction unit 150, the first estimation unit 160, and the second estimation unit 170.

The pulse wave feature extraction unit 130 extracts user's pulse wave signal features by using a user's pulse wave signal. An example of the pulse wave signal features is time-frequency features of a pulse wave signal that are calculated by wavelet transform of the pulse wave signal.

The electrocardiogram signal feature extraction unit 150 extracts user's electrocardiogram signal features by using a user's electrocardiogram signal. An example of the electrocardiogram signal features is time-frequency features of an electrocardiogram signal that are calculated by wavelet transform of the electrocardiogram signal.

The pulse wave propagation time extraction unit 140 acquires a timing of a pulse wave signal by using the user's pulse wave signal and acquires a timing of an electrocardiogram signal by using the user's electrocardiogram signal. The pulse wave propagation time extraction unit 140 acquires, as a pulse wave propagation time, a time difference between the timing of the pulse wave signal and the timing of the electrocardiogram signal. The pulse wave propagation time is a period of time taken for movement of a pulse wave between predetermined portions of a blood vessel. The pulse wave propagation time is, for example, calculated on the basis of a time difference between an a-wave of an acceleration pulse wave signal obtained by secondary differentiation of a measured plethysmogram signal and an R-wave of an electrocardiogram signal, for example, between certain portions (see, for example, Koichi FUJIMOTO, Yuji SANO, and Eiichi WATANABE "Application of Accelerated Plethysmography for Measuring Pulse Wave Velocity", Ergonomics, The Japan Ergonomics Society, Vol. 48, No. 6, pp. 285-294, 2012).

A user's pulse wave signal may include a first pulse wave signal in a first period, . . . an i-th pulse wave signal in an i-th period, . . . (i is a natural number of 1 or more). A user's electrocardiogram signal may include a first electrocardiogram signal in a first period, . . . , an i-th electrocardiogram signal in an i-th period, . . . . In a case where the i-th pulse wave signal corresponds to the i-th electrocardiogram signal, the pulse wave propagation time extraction unit 140 may (i) detect, as a first timing, a time of a peak of the i-th pulse wave signal, (ii) detects, as a second timing, a time of a peak of the i-th electrocardiogram signal, and (iii) acquire, as a pulse wave propagation time, a time difference between the first timing and the second timing.

The first estimation unit 160 estimates a user's blood pressure group by using the pulse wave signal features, the electrocardiogram signal features, and the pulse wave propagation time.

The second estimation unit 170 estimates a blood pressure value of the user 1 by using the pulse wave signal features, the electrocardiogram signal features, and the pulse wave propagation time by referring to individual estimation rules that correspond to respective blood pressure groups.

The processing circuit 101 is constituted by a processor and at least one memory. The memory stores therein processing programs for the pulse wave feature extraction unit 130, the pulse wave propagation time extraction unit 140, the electrocardiogram signal feature extraction unit 150, the first estimation unit 160, and the second estimation unit 170. The memory may also store therein the estimation rules and measurement data of the pulse wave measurement unit 110 and the electrocardiogram signal measurement unit 120.

The processor and the memory are connected by a bus, and the processor performs arithmetic processing by using the measurement data and the processing programs stored in the memory and outputs a blood pressure value. The memory may store therein the output blood pressure value.

Output Unit 180

The output unit 180 outputs information concerning a blood pressure value estimated by the processing circuit 101.

The output unit 180 may be configured as the blood pressure estimation system 10 or may be configured as a receiving device provided outside the blood pressure estimation apparatus 100. In this case, the processing circuit 101 supplies a blood pressure value to the external output unit 180. The output unit 180 acquires information concerning a blood pressure value from the processing circuit 101 and outputs the blood pressure value.

In a case where the output unit 180 is configured as the external receiving device, the processing circuit 101 and the output unit 180 include a wireless transmission module. This allows the processing circuit 101 to transmit and receive information concerning an estimated blood pressure value to and from the output unit 180.

The output unit 180 included in the blood pressure estimation system 10 is, for example, a display or a speaker. The receiving device including the output unit 180 is, for example, a smartphone, a blood pressure display device including a display, or a data accumulation server connected over the Internet.

Overall Flow

FIG. 3 illustrates a flow of an outline of overall processing of a blood pressure estimation method according to Embodiment 1.

Step S110

The pulse wave measurement unit 110 measures a pulse wave signal of the user 1. The pulse wave measurement unit 110 measures a pulse wave signal of the user 1 for a period corresponding to at least one heartbeat. The pulse wave signal of the user 1 includes information on the period corresponding to at least one heartbeat.

The pulse wave measurement unit 110 may acquire pulse wave information of the user 1 by acquiring pulse wave signals corresponding to plural heartbeats and averaging the acquired pulse wave signals. This allows the pulse wave measurement unit 110 to stably acquire pulse wave information.

Step S120

The electrocardiogram signal measurement unit 120 measures an electrocardiogram signal. Step S110 and Step S120 are performed in parallel. In other words, the pulse wave measurement unit 110 and the electrocardiogram signal measurement unit 120 measure a pulse wave signal and an electrocardiogram signal at least for the same period.

For example, upon receipt of a measurement command from the processing circuit 101, the pulse wave measurement unit 110 and the electrocardiogram signal measurement unit 120 perform measurement for a predetermined period.

Alternatively, information on a measurement period of a pulse wave signal and a measurement period of an electrocardiogram signal is stored in the memory of the blood pressure estimation apparatus 100, and the pulse wave measurement unit 110 and the electrocardiogram signal measurement unit 120 acquire information on the user 1 by referring to the information on the measurement periods stored in the memory. The measurement period of the pulse wave signal and the measurement period of the electrocardiogram signal that are stored in the memory overlap at least partially.

Step S130

The pulse wave feature extraction unit 130 extracts pulse wave signal features by using the pulse wave signal acquired in Step S110. An example of extraction of pulse wave signal features will be described later.

Step S140

The electrocardiogram signal feature extraction unit 150 extracts electrocardiogram signal features by using the electrocardiogram signal acquired in Step S120. An example of extraction of electrocardiogram signal features will be described later.

Step S150

The pulse wave propagation time extraction unit 140 extracts a pulse wave propagation time from the pulse wave signal acquired in Step S110 and the electrocardiogram signal acquired in Step S120. For example, the pulse wave propagation time extraction unit 140 extracts a pulse wave timing by using the pulse wave signal. The pulse wave propagation time extraction unit 140 extracts an electrocardiogram timing by using the electrocardiogram signal.

Step S160

The first estimation unit 160 estimates a blood pressure group of the user by using the pulse wave signal features, the electrocardiogram signal features, and the pulse wave propagation time.

Step S170

The second estimation unit 170 estimates a blood pressure value of the user 1 by using the pulse wave signal and the electrocardiogram signal while referring to the individual estimation rules corresponding to the respective blood pressure groups. The processing from Step S130 to Step S170 is also referred to as blood pressure estimation processing S101.

Step S180

The output unit 180 outputs the blood pressure value estimated in Step S170.

Through the above flow, a blood pressure estimation result based on data obtained by each measurement can be calculated.

Experiment for Acquisition of Data for Evaluation

The inventors of the present invention conducted an experiment for acquisition of data for evaluation in order to evaluate operation of the blood pressure estimation apparatus 100. Details of the blood pressure estimation processing S101 and a processing result of data are described by using this data.

In the experiment, 97 subjects were examined. Before the experiment, informed consent was obtained from the subjects.

Electrocardiogram data and pulse wave data of the subjects were measured by using a small-size sensor module. The small-size sensor module is capable of concurrently measuring an electrocardiogram signal and a pulse wave signal. Furthermore, blood pressure values of the subjects were measured by using a commercially available cuff-type sphygmomanometer.

FIG. 4 illustrates a flow of acquisition of data of a single subject. As for a measurement procedure, the international standards for non-invasive sphygmomanometers (IEC 80601-2-30: 2009, Medical electrical equipment—Part 2-30: Particular requirements for basic safety and essential performance of automated non-invasive sphygmomanometers) were referred to.

Step S121

The subject was kept at rest for five minutes in order to acquire stable data.

Step S122

A blood pressure value of the subject was measured by using a reference sphygmomanometer. The blood pressure value measured by using the reference sphygmomanometer was used as a basis of blood pressure data for creation of an estimation formula. A commercially available cuff-type sphygmomanometer was used as the reference sphygmomanometer. It is estimated that a similar result is obtained even in a case where a blood pressure value is measured by using other reference blood pressure measurement methods such as a method using a cuff-type mercury sphygmomanometer performed by a laboratory technician.

Step S123

The subject was kept at rest for one minute. One minute was set as a period that is necessary for stabilization of data after switching from measurement of a blood pressure value by the cuff-type to measurement of a pulse wave signal and an electrocardiogram signal.

Step S124

Figure 5A:
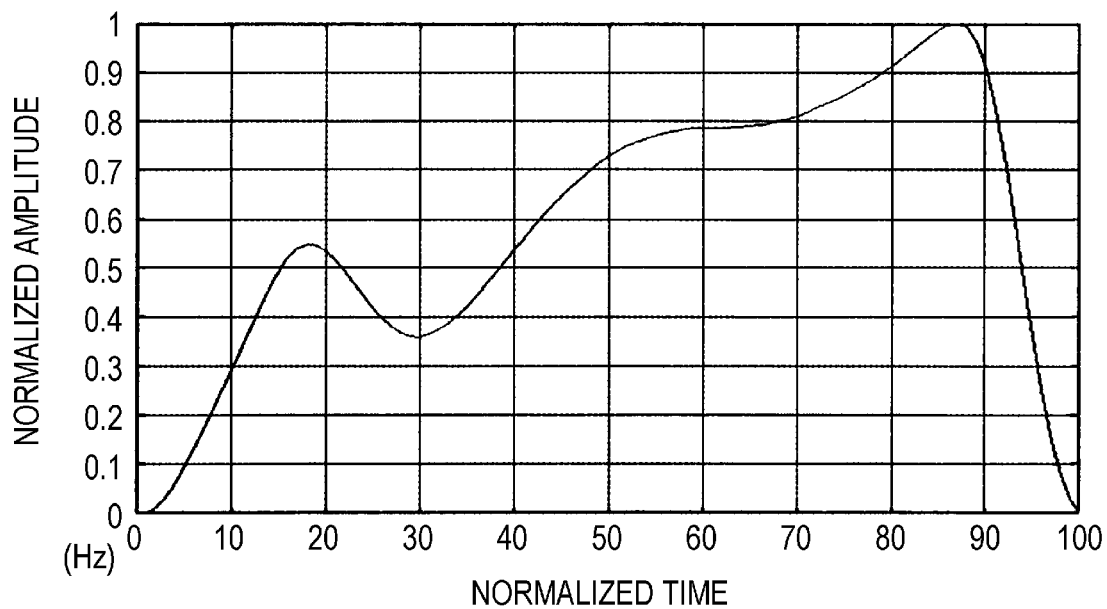
FIG. 5A illustrates an example of a measured waveform of a pulse wave signal.
Figure 5B:
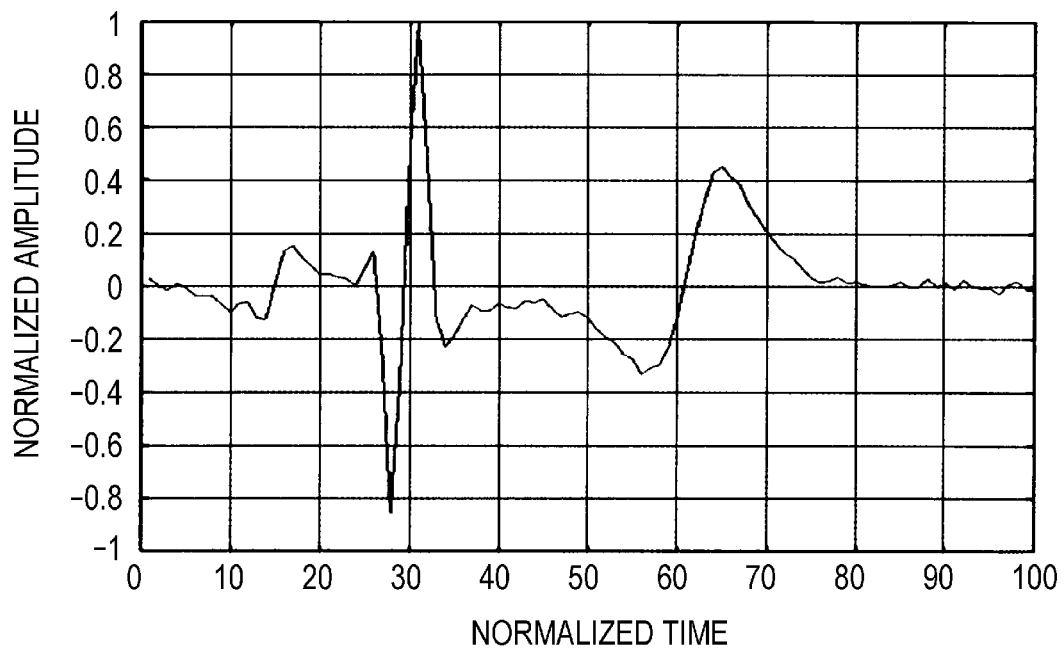
FIG. 5B illustrates an example of a measured waveform of an electrocardiogram signal.

An electrocardiogram signal and a pulse wave signal were concurrently measured. FIG. 5A illustrates a waveform of the measured pulse wave signal, and FIG. 5B illustrates a waveform of the measured electrocardiogram signal.

Step S125

The subject was kept at rest for one minute. One minute was set as a period that is necessary for stabilization of data after switching from measurement of a pulse wave signal and an electrocardiogram signal to measurement of a blood pressure value by the cuff-type.

Step S126

A blood pressure value of the subject was measured by using the reference sphygmomanometer. This blood pressure value was used for a basis of blood pressure data for machine learning.

Step S127

It was determined whether or not a predetermined number of pieces (times) of data was acquired. In a case of NO, the processing proceeds to Step S123. In a case of YES, data acquisition is finished. In this experiment, acquisition of three pieces (three times) of data was set as a condition for completion.

Measurement of blood pressure using the commercially available cuff-type sphygmomanometer and acquisition of pulse wave data and electrocardiogram data were alternately performed in accordance with the flow of FIG. 4. Since there is a possibility that blood pressure fluctuate with passage of time, a correct blood pressure value corresponding to the acquired pulse wave data and electrocardiogram data was calculated by averaging values measured by using the reference sphygmomanometer at preceding and succeeding timings. In a case where there is a large difference between the values measured by using the reference sphygmomanometer at the preceding and succeeding timings, these values were regarded as data obtained in the middle of fluctuation of blood pressure and excluded from data for creation of an estimation formula.

Acquired Data

FIG. 5A illustrates a waveform of the measured pulse wave signal (hereinafter also referred to as a pulse wave waveform). FIG. 5B illustrates an example of a waveform of the measured electrocardiogram signal (hereinafter also referred to as an electrocardiogram waveform). FIGS. 5A and 5B illustrate waveforms obtained by normalizing the pulse wave waveform and the electrocardiogram waveform, respectively. In FIGS. 5A and 5B, the vertical axis represents an amplitude of a waveform, and the horizontal axis represents time.

Figure 6A:
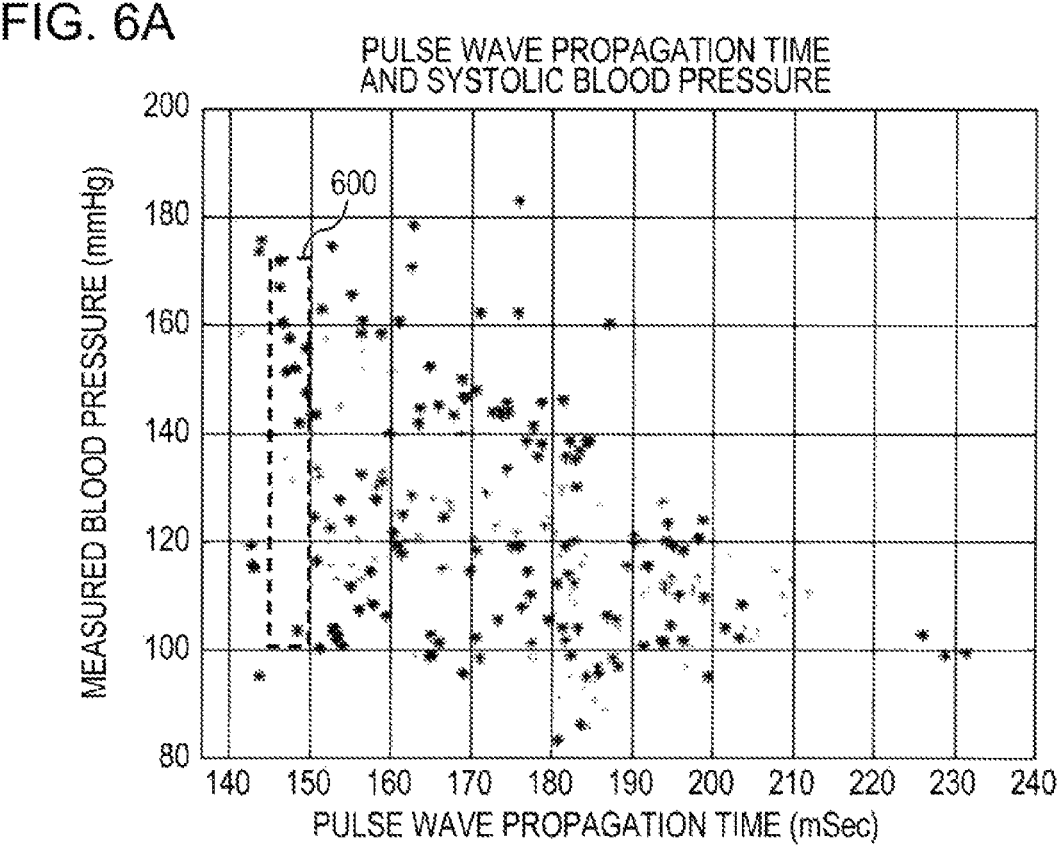
FIG. 6A illustrates a relationship between blood pressure values and pulse wave propagation times.

FIG. 6A illustrates a relationship between a pulse wave propagation time and a systolic blood pressure value. In FIG. 6A, the horizontal axis represents a pulse wave propagation time calculated from measurement data, and the vertical axis represents a systolic blood pressure value corresponding to the measurement data. The plots in FIG. 6A were created from the acquired measurement data.

In FIG. 6A, a tendency corresponding to medical knowledge that a high blood pressure value is obtained in a case where a pulse wave propagation time is short can be seen. However, FIG. 6A shows that systolic blood pressure values corresponding to points having an identical pulse wave propagation time are distributed in a wide range. Specifically, a region 600 surrounded by the dotted line in FIG. 6A includes points that have pulse wave propagation times in a range from approximately 145 mSec to 150 mSec and blood pressure values in a range from approximately 100 mmHg to 170 mmHg. That is, variation of blood pressure values is very large as compared with variation of pulse wave propagation times.

In a case where a linear regression formula (an estimated value of systolic blood pressure=a*1/pulse wave propagation time+b; a and b are constants set on the basis of acquired data) for blood pressure estimation using a pulse wave propagation time was created for the data in FIG. 6A, a standard deviation of errors was 18.24 mmHg. The international standards for cuff-type non-invasive sphygmomanometers require that a standard deviation of errors be 8 mmHg or less. That is, according to the method using a pulse wave propagation time, a standard deviation of errors is large.

Details of Blood Pressure Estimation Processing S101

Next, details of the blood pressure estimation processing S101 from Step S130 to Step S170 in FIG. 3 are described.

Extraction of Features: Extraction of Pulse Wave Signal Features and Extraction of Electrocardiogram Signal Features The pulse wave features extraction processing in Step S130 and the electrocardiogram signal features extraction processing in Step S140 are described below. Both a pulse wave signal and an electrocardiogram signal are extracted as an electric fluctuation.

In this experiment, data to be analyzed (waveforms at 1024 Hz for ten seconds) was acquired. Since the data to be analyzed includes a plurality of heartbeats, waveforms corresponding to a single beat were extracted from the data to be analyzed on the basis of a peak of an R-wave of the electrocardiogram signal. That is, a plurality of waveforms were extracted from the data to be analyzed. Since a heartbeat interval varies depending on a heart rate, the extracted plurality of waveforms corresponding to a single beat were normalized, and then arithmetic mean of the plurality of waveforms was obtained. This makes it possible to reduce the influence of fluctuation in a specific part. Two arithmetic mean waveforms corresponding to a pulse wave signal and an electrocardiogram signal were created, and wavelet features of the waveforms were calculated. In a time direction, the normalized time corresponding to a single beat was divided into 20 sections. The frequency was divided into 8 sections on the basis of a maximum frequency 40 Hz. Wavelet features for each cell were calculated.

In Step S150, a pulse wave propagation time was calculated by using a time difference between a peak of a pulse wave signal and a peak of an electrocardiogram signal.

As a result of the processes in Steps S130, S140, and S150, a lot of candidates features derived from the pulse wave waveform and/or the electrocardiogram waveform are prepared in addition to the pulse wave propagation time. Conventionally, a blood pressure value is sometimes estimated by using a pulse wave propagation time. Improvement of accuracy of blood pressure value estimation can be anticipated by using these waveform features.

Description About First Estimation Unit 160

Next, details of processing performed in Step S160 by the first estimation unit 160 are described. The first estimation unit 160 estimates a blood pressure group by using pulse wave signal features, electrocardiogram signal features, and a pulse wave propagation time. The blood pressure group is a group derived from a relationship between pulse wave propagation times and blood pressure values. For example, grouping is performed on the basis of whether points having the same pulse wave propagation time have a high blood pressure value or a low blood pressure value.

It is generally said that there is high correlation between a pulse wave propagation time and blood pressure. However, the inventors of the present invention revealed by an experiment that blood pressure values that correspond to the same pulse wave propagation time range widely. That is, the inventors of the present invention revealed that estimation accuracy is not high in a case where a blood pressure value is estimated on the basis of a pulse wave propagation time.

It may be possible to employ a method for measuring a user's blood pressure value in advance by using a cuff type and then determining a user's group on the basis of the blood pressure value. However, in the blood pressure estimation apparatus 100, a user's blood pressure group is estimated by using user's pulse wave signal features, electrocardiogram signal features, and a pulse wave propagation time instead of the method for measuring a user's blood pressure value in advance by using a cuff type and then determining a user's group on the basis of the blood pressure value.

The first estimation unit 160 estimates a blood pressure group by using features included in feature candidate group obtained in Steps S130, S140, and S150.

The second estimation unit 170 estimates blood pressure by referring to a standard corresponding to the blood pressure group. An example of the standard corresponding to the blood pressure group is a blood pressure value estimation formula for each group. In this way, it is possible to increase accuracy of estimation of a blood pressure value.

The idea of grouping is described below. The inventors of the present invention conducted a follow-up survey on a change in pulse wave propagation time in a case where blood pressure of an individual fluctuates. As a result, the inventors of the present invention found that the tendency of the relationship between a change in pulse wave propagation time and a blood pressure value is kept even in a case where blood pressure fluctuates. A similar tendency was seen both in a case where a blood pressure value is high and in a case where a blood pressure value is low.

Figure 6B:
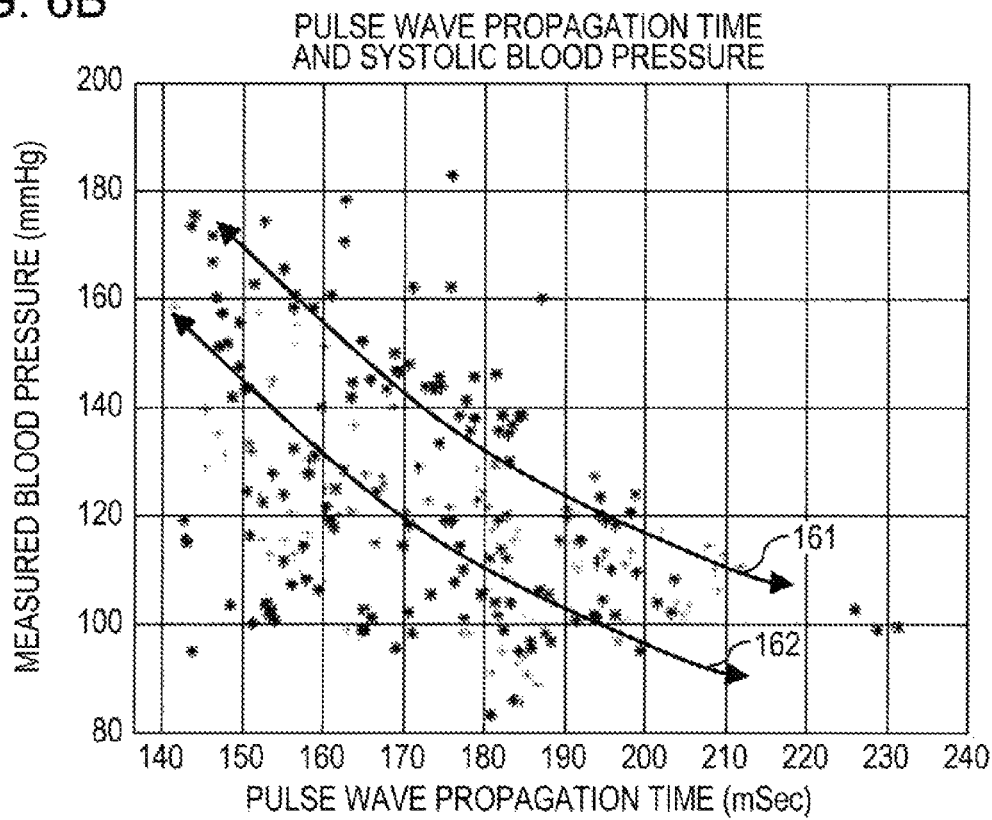
FIG. 6B illustrates a relationship between blood pressure values and pulse wave propagation times.

Changes of a pulse wave propagation time and a blood pressure value are described below with reference to FIG. 6B. FIG. 6B schematically illustrates changes of a pulse wave propagation time and a blood pressure value. The line 161 illustrated in FIG. 6B indicates changes of a pulse wave propagation time and a blood pressure value of a person having a high blood pressure value. The line 162 illustrated in FIG. 6B indicates changes of a pulse wave propagation time and a blood pressure value of a person having a low blood pressure value. That is, FIG. 6B shows that the blood pressure value of the person having tendency indicated by the line 161 and the blood pressure value of the person having tendency indicated by the line 162 are markedly different from each other even in a case where the same pulse wave propagation time is measured.

Based on this tendency, the inventors of the present invention thought that a pulse wave waveform or an electrocardiogram waveform includes not only information related to a blood pressure value itself, but also information reflecting a relationship between a pulse wave propagation time and a blood pressure value. In view of this, the first estimation unit 160 is provided before estimation of a blood pressure value. For this reason, the first estimation unit is designed to estimate not a blood pressure value, but a blood pressure group in order to estimate a relationship like the one illustrated in FIG. 6B. It is also effective to estimate whether blood pressure tends to be high or low.

Figure 8:
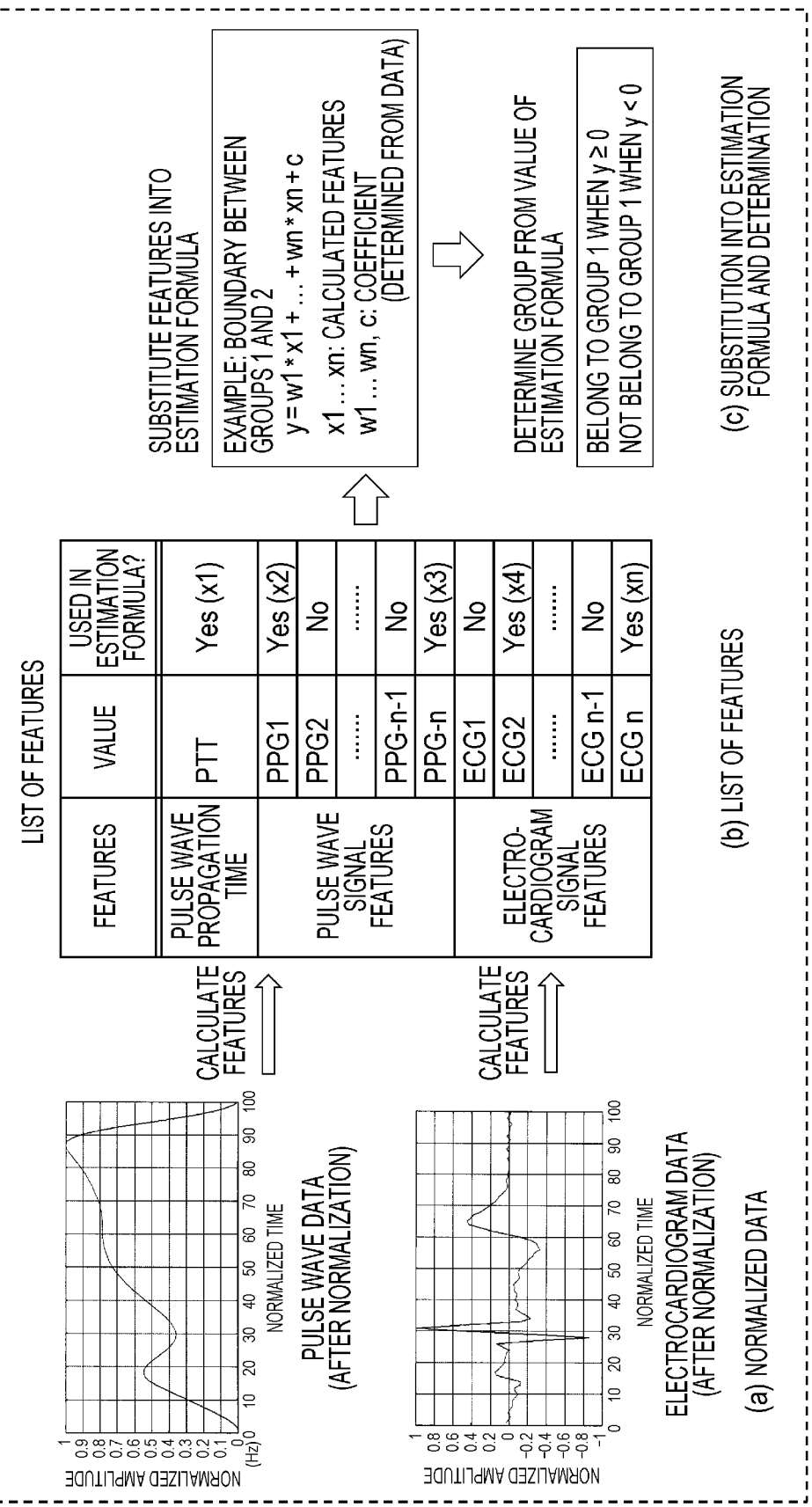
FIG. 8 schematically illustrates a flow of processing performed by the first estimation unit.

FIG. 7 illustrates a processing flow of the first estimation unit 160. FIG. 8 schematically illustrates a flow of processing performed by the first estimation unit 160.

Step S161

The first estimation unit 160 acquires pulse wave signal features extracted in Step S130.

Step S162

The first estimation unit 160 acquires electrocardiogram signal features extracted in Step S140.

Step S163

The first estimation unit 160 acquires a pulse wave propagation time extracted in Step S150.

Steps S161 through S163 need not necessarily be performed in this order. It is only necessary that the first estimation unit 160 acquire pulse wave signal features, electrocardiogram signal features, and a pulse wave propagation time.

In these steps (Steps S161 through S163), the first estimation unit 160 acquires features including normalized pulse wave data and electrocardiogram data ((a) of FIG. 8). (b) of FIG. 8 illustrates the acquired features, i.e., the pulse wave signal features, the electrocardiogram signal features, and the pulse wave propagation time. Note that the features are the pulse wave signal features and/or the electrocardiogram signal features and/or the pulse wave propagation time.

Step S164

The first estimation unit 160 selects at least one feature from a group consisting of the pulse wave signal features, the electrocardiogram signal features, and the pulse wave propagation time by referring to an estimation rule for estimating a group showing relevance between a pulse wave propagation time and a blood pressure value. An example of the rule is an estimation formula or an estimation table. The estimation formula is a formula for finding a group on the basis of the pulse wave signal features, the electrocardiogram signal features, and the pulse wave propagation time. The estimation table is a table in which the pulse wave signal features, the electrocardiogram signal features, and the pulse wave propagation time are associated with groups.

In (b) of FIG. 8, n features x1 through xn are selected from a set of features used for an estimation formula set in advance from data for learning. The pulse wave signal features and the electrocardiogram signal features are, for example, time-frequency features.

Step S165

The first estimation unit 160 estimates a group by using the selected features and the estimation rule. Specifically, the first estimation unit 160 calculates a blood pressure group number by substituting the features into the estimation formula.

(c) of FIG. 8 illustrates an example of a formula corresponding to a boundary between a group 1 and a group 2. In (c) of FIG. 8, x1 through xn are features received in Step S163, and w1 through wn and c are constants that are determined in advance from the learning data and are multiplied with the features.

A group number is determined depending on whether a calculation result y of this formula is positive or negative. Since there are five groups, a group to which measurement data obtained this time belongs is finally determined by performing similar calculation for each boundary.

Step S166

The first estimation unit 160 outputs the group number calculated in Step S165 and then finishes the processing.

Creation of Estimation Rule for First Estimation Unit

A method for creating an estimation rule used by the first estimation unit 160 is described with reference to FIG. 9.

Data indicating a relationship between pulse wave propagation times and blood pressure values obtained in FIG. 6B is divided into groups depending on plotted positions thereof.

Figure 9:
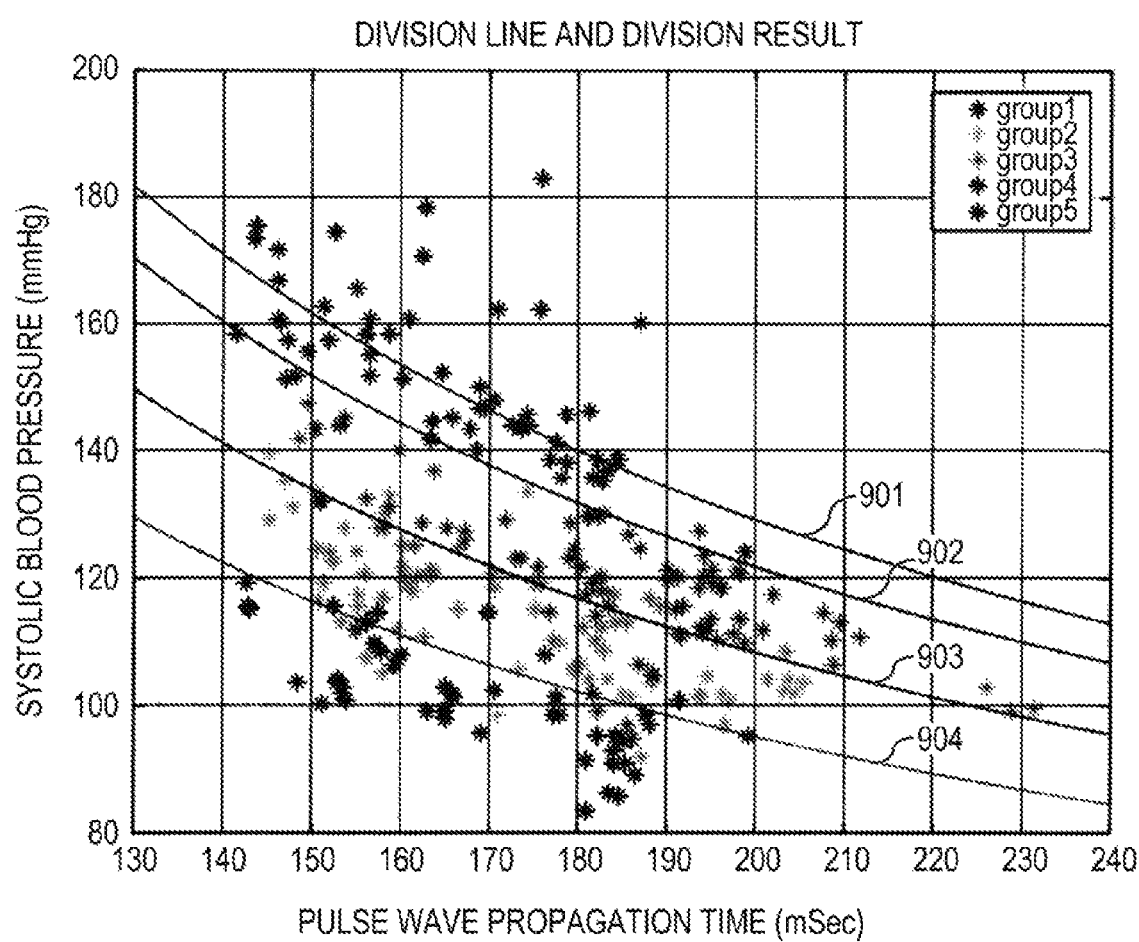
FIG. 9 illustrates a result of grouping based on an estimation formula of the first estimation unit.

In the example of FIG. 9, the data is divided into five blood pressure groups (group 1 through group 5). The four lines (lines 901 through 904) illustrated in FIG. 9 indicate boundaries between groups. For example, the boundaries between the groups are set so that a predetermined percentage of measurement data points are included in each group. Specifically, the data is divided into the group 1 having blood pressure values higher than the boundary 901, the group 2 having blood pressure values between the boundary 901 and the boundary 902, the group 3 having blood pressure values between the boundary 902 and the boundary 903, the group 4 having blood pressure values between the boundary 903 and the boundary 904, and the group 5 having blood pressure values lower than the boundary 904.

In a case where an estimation rule by which each measurement point is classified into a blood pressure group can be created, such an estimation rule can be used as an estimation rule for the first estimation unit 160.

Learning data is prepared for creation of an estimation formula. A correct group number is assigned to each data point. The estimation formula is expressed, for example, by a linear sum of the features used in Step S161 through Step S163, and a coefficient is set so that a correct group number is output for each data point. Since the number of features is large, selection of a variable is also effective. The variable can be selected, for example, by using a forward selection method. In this method, for example, 10 variables are selected from among several hundreds of feature candidates. This number need just be determined in view of calculation load, accuracy, and the like. Specifically, the inventors of the present invention set a user's blood pressure group by using pulse wave signal features, electrocardiogram signal features, and a pulse wave propagation time instead of acquiring a blood pressure value in advance and then acquiring a user's group.

Through the above processing, a group that is related to whether blood pressure is high relative to a pulse wave propagation time is estimated for measurement data obtained this time. Therefore, the first estimation unit 160 can obtain a blood pressure group by using time-frequency features of a pulse wave signal, time-frequency features of an electrocardiogram signal, and a pulse wave propagation time by referring to an estimation rule.

Although there are five blood pressure groups in FIG. 9, estimation of a blood pressure value can be improved as long as there are at least two blood pressure groups. The blood pressure groups are, for example, a first group having high blood pressure values and a second group having low blood pressure values. The first group has points having blood pressure values that are higher than a first blood pressure value. The second group has points having blood pressure values that are equal to or lower than the first blood pressure value.

Description about Second Estimation Unit

Figure 10:
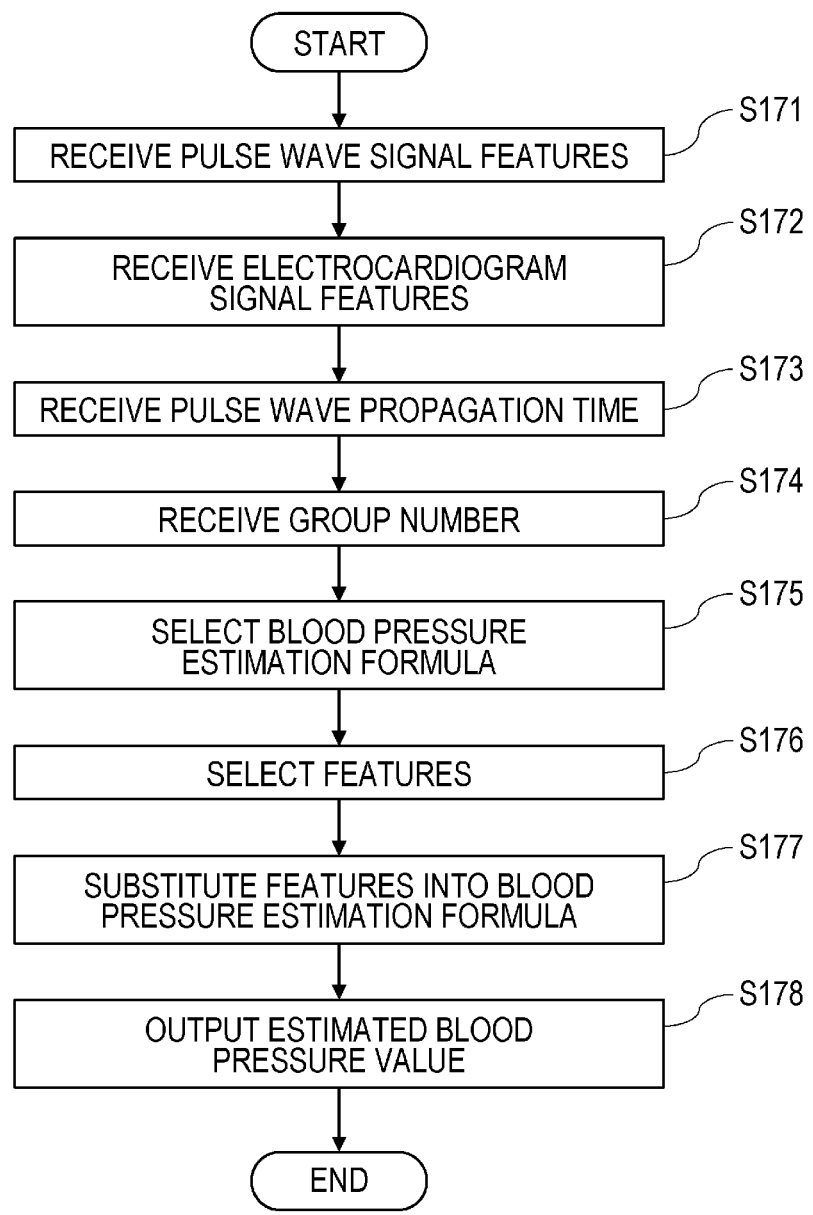
FIG. 10 illustrates a processing flow of a second estimation unit.

Next, details of processing performed in Step S170 by the second estimation unit 170 are described. The second estimation unit 170 estimates a blood pressure value by using an estimation rule prepared for each blood pressure group. FIG. 10 illustrates a processing flow of the second estimation unit 170.

Step S171

The second estimation unit 170 acquires the pulse wave signal features extracted in Step S130.

Step S172

The second estimation unit 170 acquires the electrocardiogram signal features extracted in Step S140.

Step S173

The second estimation unit 170 acquires the pulse wave propagation time extracted in Step S150.

Step S174

The second estimation unit 170 acquires a blood pressure group (e.g., a group number) calculated in Step S160.

Step S175

The second estimation unit 170 acquires an estimation rule corresponding to the group number received in Step S174. The blood pressure estimation rule is, for example, stored in a database of the blood pressure estimation apparatus 100. Alternatively, the estimation rule may be stored in a database provided outside the blood pressure estimation apparatus 100, and the second estimation unit 170 may acquire the estimation rule wirelessly or through a wire. An example of the estimation rule is an estimation formula or an estimation table. The estimation formula is a formula in which pulse wave signal features, electrocardiogram signal features, and a pulse wave propagation time are used as variables and by which a solution of a blood pressure value is obtained. The estimation table is a table in which blood pressure values are associated with the pulse wave signal features, the electrocardiogram signal features, and the pulse wave propagation time.

The estimation formula is set for each blood pressure group, and each estimation formula performs calculation for blood pressure estimation based on necessary features.

Step S176

The second estimation unit 170 selects features included in the estimation rule selected in Step S175 from among feature candidates acquired in Step S171 through Step S173.

Step S177

The second estimation unit 170 calculates an estimated blood pressure value by using the selected features and estimation formula.

Step S178

The second estimation unit 170 outputs the estimated blood pressure value calculated in Step S177.

Through the above processing, blood pressure is estimated by a blood pressure value estimation formula for each blood pressure group to which measurement data obtained this time is estimated to belong.

Creation of Estimation Rule for Second Estimation Unit 170

A method for creating an estimation rule for the second estimation unit 170 is described below with reference to FIG. 11. An example of an estimation formula is described as the estimation rule. As illustrated in FIG. 11, each group includes a plurality of measurement data points and includes various pulse wave propagation times and correct blood pressure values. The second estimation unit 170 creates different estimation formulas for respective groups. In this example, since there are five groups, five estimation formulas are created.

Learning data is prepared for creation of an estimation formula. An estimation formula is created so that reference blood pressure values are correct for measurement data having the same group number.

The estimation formula is expressed, for example, by a linear sum of the features used in Step S171 through Step S173, and a coefficient of the estimation formula is set so that a correct blood pressure value is output for each data point. Since the number of features is large, selection of a variable is also effective. The variable can be selected, for example, by using a forward selection method. In this method, for example, 10 variables are selected from among several hundreds of feature candidates. This number need just be determined in view of calculation load, accuracy, and the like. This estimation formula is created for each group number. Since the variables are individually selected so that errors are small in the estimation formula in the first estimation unit 160 and the estimation formulas in the second estimation unit 170, it is assumed that different results are obtained. This is considered to reflect characteristics of a person having high blood pressure or a person having low blood pressure.

Example of Division in Second Estimation Unit 170

FIG. 11 illustrates an example of linear formulas for respective groups. As is clear from FIG. 11, groups can be estimated from waveform features by using formulas for linear regression corresponding to the respective five groups.

Example of Estimation Result

A standard deviation of errors between estimation results and measurement results was found in order to evaluate the estimation method.

Figure 12A:
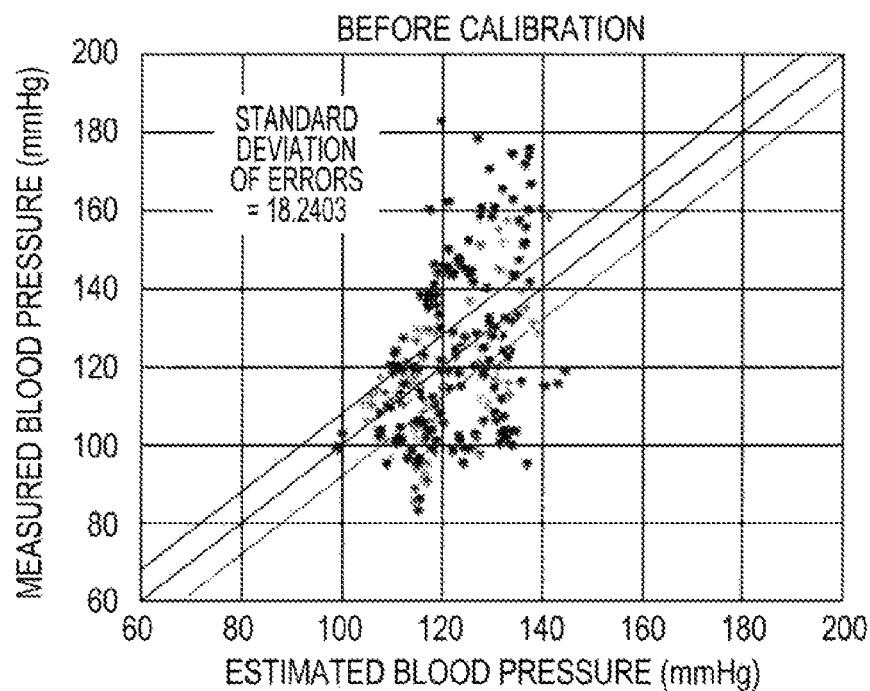
FIG. 12A illustrates a distribution of blood pressure values estimated by a conventional method and actual measurement values.
Figure 12B:
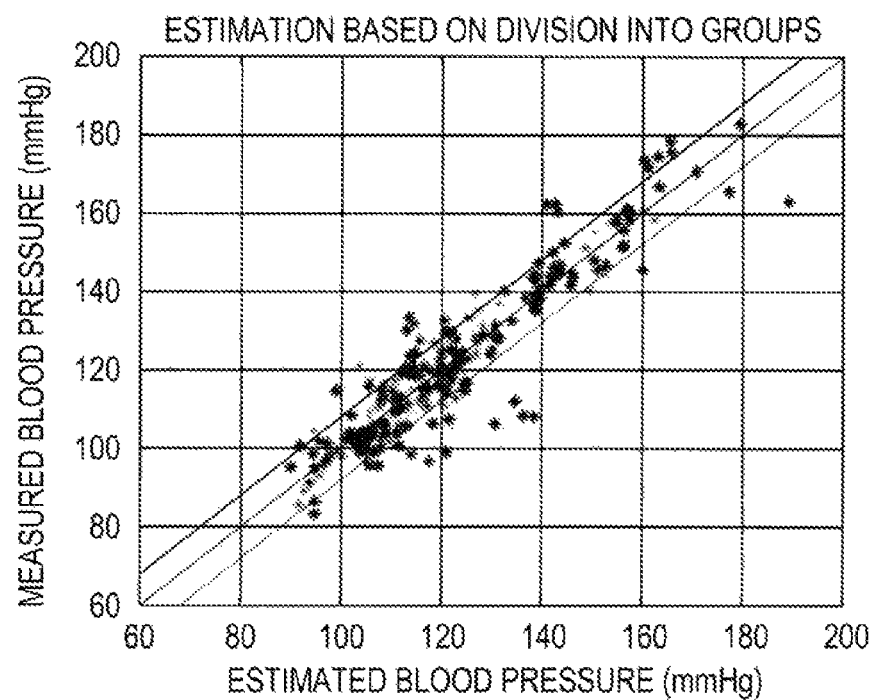
FIG. 12B illustrates a distribution of blood pressure values estimated by the present estimation method and actual measurement values.

FIGS. 12A and 12B illustrate evaluation results of errors between estimated values and actual measurement values. FIG. 12A illustrates a result obtained in a case where a pulse wave propagation time is used (a conventional method). FIG. 12B illustrates an estimation result obtained in a case where the method according to the present embodiment is employed.

In a case where learning data used for creation of an estimation formula and evaluation data were identical in the data of FIG. 12B, a standard deviation of errors was 7.64 mmHg. In a case where the learning data and the evaluation data were different, a standard deviation of errors obtained by cross-validation was 11.41 mmHg.

Other Examples of Estimation Method

In the present embodiment, an example in which the estimation formulas in the first estimation unit 160 and the second estimation unit 170 are created by linear discrimination has been described. However, any general pattern classifier is applicable. What is important in this case is to define input data as learning data and a target value, and this part may be similar to the method described in the present embodiment. As the pattern classifier, a non-linear classifier such as a support vector machine and/or a method based on a neural network such as deep learning are also effective for improvement of accuracy.

In the present embodiment, for example, wavelet features calculated from a shape of a pulse wave waveform are used as features in the pulse wave feature extraction unit. However, an acceleration pulse wave is also effective. Improvement of accuracy can be anticipated by adding, as candidates, wavelet features of a parameter of a wave height of an acceleration pulse wave and/or a waveform of the acceleration pulse wave.

Effects

According to the above configuration, in which a group reflecting user's blood pressure characteristics is first estimated by the first estimation unit and then a regression formula created for each group is applied in the second estimation unit, accuracy of estimation of a blood pressure value can be increased. According to the configuration, a range covered by a single regression method is narrow, and the covered range matches blood pressure characteristics.

This improves accuracy of regression, resulting in improvement of blood pressure estimation accuracy.

According to medical knowledge and as is generally known as knowledge concerning health, blood pressure tends to become higher with increasing age. In view of this, it may be possible to employ grouping based on users' ages instead of grouping based on users' blood pressure characteristics in the above blood pressure estimation method. However, in a case where there are large differences in blood pressure characteristics among users in close generations, it is impossible to accurately estimate blood pressure by employing grouping based on ages, as in the case of regression of blood pressure estimation based on a pulse wave propagation time.

Figure 13:
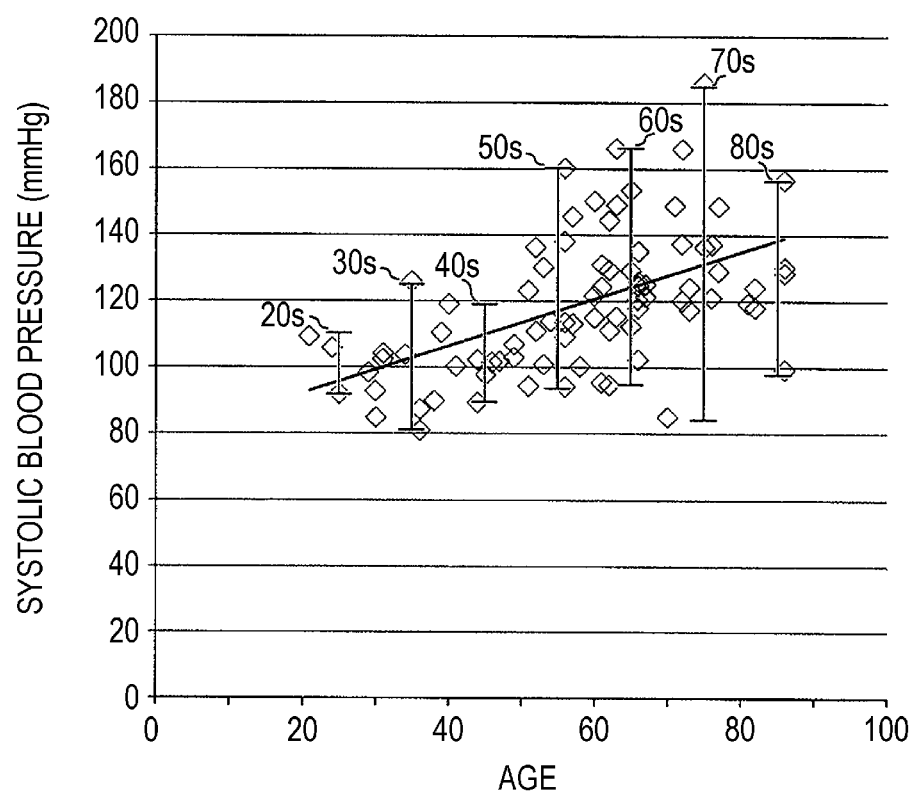
FIG. 13 illustrates a relationship between blood pressure values and ages.

Whether grouping based on ages is appropriate or not is verified by referring to actual blood pressure data. FIG. 13 is a graph illustrating correlation between age and systolic blood pressure. This data is based on a result of blood pressure measurement conducted on 84 men and women in their twenties to eighties. The vertical lines given reference signs indicative of generations each indicate a width between a maximum value and a minimum value in the generation.

It can be seen from the data as a whole that blood pressure tends to increase with increasing age as indicated by a regression line in the graph. A width of systolic blood pressure values in each generation is relatively small (a little less than 20 mmHg) in the twenties. However, for example, the difference is close to 70 mmHg indicated by the broken-like frame in FIG. 6A in the fifties and the sixties, and the difference is 100 mmHg in the seventies. Since there are large differences among individuals in older ages in which blood pressure management is especially needed, the blood pressure estimation approach based on ages has a large estimation error. Therefore, according to grouping in the blood pressure estimation method according to the present embodiment, blood pressure can be estimated with higher accuracy than grouping based on generations.

In the present disclosure, all or a part of any of unit, device, part or portion, or any of functional blocks in the block diagram illustrated in FIG. 1 may be implemented as one or more of electronic circuits including a semiconductor device, a semiconductor integrated circuit (IC) or a large scale integration (LSI). The LSI or IC can be integrated into one chip, or also can be a combination of plural chips. For example, functional blocks other than a memory may be integrated into one chip. The name used here is LSI or IC, but it may also be called system LSI, very large scale integration (VLSI), or ultra large scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can be used for the same purpose.

Furthermore, it is also possible that all or a part of the functions or operations of the unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

A blood pressure estimation apparatus, a blood pressure estimation method, and a non-transitory computer-readable recording medium according to the present disclosure are useful for estimation of a blood pressure value in a cuffless blood pressure estimation system. The blood pressure estimation apparatus, the blood pressure estimation method, and the non-transitory computer-readable recording medium according to the present disclosure can also be used, for example, for continuous estimation of a blood pressure value and/or simplified estimation of a blood pressure value not only in a hospital but also in various daily-life situations, for example, at home and/or a workplace since measurement of a pulse wave signal and an electrocardiogram signal, which is needed in this method, causes less burden on a subject.

What is claimed is:

1. A blood pressure estimation apparatus comprising:
a processing circuit that estimates a blood pressure value of the user by using a pulse wave signal of the user acquired from a pulse wave sensor and an electrocardiogram signal of the user acquired from an electrocardiogram sensor,
wherein the processing circuit (a) acquires a pulse wave signal feature by using the pulse wave signal of the user, the pulse wave signal feature being a time-frequency feature of the pulse wave signal, (b) acquires an electrocardiogram signal feature by using the electrocardiogram signal of the user, the electrocardiogram signal feature being a time-frequency feature of the electrocardiogram signal, (c) acquires a pulse wave propagation time by using the pulse wave signal of the user and the electrocardiogram signal of the user, (d) selects a blood pressure group by using the pulse wave signal feature, the electrocardiogram signal feature, and the pulse wave propagation time, the blood pressure group being indicative of a relationship between a pulse wave propagation time and blood pressure of the user, and (e) estimates the blood pressure value of the user by using the blood pressure group, the pulse wave signal feature, the electrocardiogram signal feature, and the pulse wave propagation time.

2. The blood pressure estimation apparatus according to claim 1, wherein
the blood pressure group includes a first group having a first blood pressure value with respect to the pulse wave propagation time and a second group having a blood pressure value lower than the first blood pressure value with respect to the pulse wave propagation time; and
in (d), the processing circuit selects the first group or the second group by using the pulse wave signal feature, the electrocardiogram signal feature, and the pulse wave propagation time.

3. The blood pressure estimation apparatus according to claim 1, wherein
the processing circuit acquires a pulse wave wavelet feature by using the pulse wave signal of the user in (a) and acquires an electrocardiogram wavelet feature by using the electrocardiogram signal of the user in (b).

4. The blood pressure estimation apparatus according to claim 1, wherein
the processing circuit acquires a pulse wave wavelet feature by using a pulse wave waveform corresponding to a single heartbeat of the user in (a) and acquires an electrocardiogram wavelet feature by using an electrocardiogram waveform corresponding to a single heartbeat of the user in (b).

5. The blood pressure estimation apparatus according to claim 1, wherein
in (e), the processing circuit acquires an estimation rule corresponding to the blood pressure group and estimates the blood pressure value of the user by using the estimation rule, the pulse wave signal feature, the electrocardiogram signal feature, and the pulse wave propagation time.

6. The blood pressure estimation apparatus according to claim 5, wherein
the estimation rule is an estimation formula using the pulse wave signal feature, the electrocardiogram signal feature, and the pulse wave propagation time as variables; and
in (e), the processing circuit estimates the blood pressure value of the user by using the pulse wave signal feature, the electrocardiogram signal feature, and the pulse wave propagation time while referring to the estimation formula.

7. The blood pressure estimation apparatus according to claim 1, further comprising a device that outputs the estimated blood pressure value.

8. A non-transitory computer-readable recording medium storing a program for causing a computer to:
(f1) acquire a pulse wave signal of a user from a pulse wave sensor and acquire an electrocardiogram signal of the user from an electrocardiogram sensor,
(f2) acquire a pulse wave signal feature by using the pulse wave signal of the user, the pulse wave signal feature being a time-frequency feature of the pulse wave signal,
(f3) acquire an electrocardiogram signal feature by using the electrocardiogram signal of the user, the electrocardiogram signal feature being a time-frequency feature of the electrocardiogram signal
(f4) acquire a pulse wave propagation time by using the pulse wave signal of the user and the electrocardiogram signal of the user,
(f5) select a blood pressure group by using the pulse wave signal feature, the electrocardiogram signal feature, and the pulse wave propagation time, the blood pressure group being indicative of a relationship between a pulse wave propagation time and blood pressure of the user, and
(f6) estimate a blood pressure value of the user by using the blood pressure group, the pulse wave signal feature, the electrocardiogram signal feature, and the pulse wave propagation time.

9. The non-transitory computer-readable recording medium according to claim 8, wherein
the blood pressure group includes a first group having a first blood pressure value with respect to the pulse wave propagation time and a second group having a blood pressure value lower than the first blood pressure value with respect to the pulse wave propagation time; and
in (f5), the first group or the second group is selected by using the pulse wave signal feature, the electrocardiogram signal feature, and the pulse wave propagation time.

10. The non-transitory computer-readable recording medium according to claim 8, wherein
a pulse wave wavelet feature is acquired by using a pulse wave waveform corresponding to a single heartbeat of the user in (f2); and
an electrocardiogram wavelet feature is acquired by using an electrocardiogram waveform corresponding to a single heartbeat of the user in (f3).

11. The non-transitory computer-readable recording medium according to claim 8, wherein
in (f6), an estimation rule corresponding to the blood pressure group is acquired, and the blood pressure value of the user is estimated by using the estimation rule, the pulse wave signal feature, the electrocardiogram signal feature, and the pulse wave propagation time.

12. The non-transitory computer-readable recording medium according to claim 11, wherein
the estimation rule is an estimation formula using the pulse wave signal feature, the electrocardiogram signal feature, and the pulse wave propagation time as variables; and
in (f6), the blood pressure value of the user is estimated by using the pulse wave signal feature, the electrocardiogram signal feature, and the pulse wave propagation time while referring to the estimation formula.

13. The non-transitory computer-readable recording medium according to claim 8, further causing the computer to (f7) output the estimated blood pressure value.

14. A blood pressure estimation method comprising:
(f1) acquiring a pulse wave signal of a user from a pulse wave sensor and acquiring an electrocardiogram signal of the user from an electrocardiogram sensor;
(f2) acquiring a pulse wave signal feature by using the pulse wave signal of the user;
(f3) acquiring an electrocardiogram signal feature by using the electrocardiogram signal of the user;
(f4) acquiring a pulse wave propagation time by using the pulse wave signal of the user and the electrocardiogram signal of the user;
(f5) selecting a blood pressure group by using the pulse wave signal feature, the electrocardiogram signal feature, and the pulse wave propagation time, the blood pressure group being indicative of a relationship between a pulse wave propagation time and blood pressure of the user; and
(f6) estimating a blood pressure value of the user by using the blood pressure group, the pulse wave signal feature, the electrocardiogram signal feature, and the pulse wave propagation time.

* * * * *